(12) United States Patent
Yagita

(10) Patent No.: US 6,914,672 B2
(45) Date of Patent: Jul. 5, 2005

(54) INSPECTING APPARATUS FOR FOREIGN MATTER AND INSPECTING MECHANISM THEREOF

(75) Inventor: Kiyoshi Yagita, Tokyo (JP)

(73) Assignee: Scan Technology Co., Ltd., Tokyo (JP)

(*) Notice: Subject to any disclaimer, the term of this patent is extended or adjusted under 35 U.S.C. 154(b) by 275 days.

(21) Appl. No.: 10/251,234

(22) Filed: Sep. 19, 2002

(65) Prior Publication Data

US 2003/0210397 A1 Nov. 13, 2003

(30) Foreign Application Priority Data

May 13, 2002 (JP) ........................................ 2002-137288

(51) Int. Cl.$^7$ .............................................. G01N 21/90
(52) U.S. Cl. ................................. 356/239.5; 250/223 B
(58) Field of Search .......................... 356/239.4–239.6, 356/240.1, 335, 336, 427, 436; 250/559.41, 223 B

(56) References Cited

U.S. PATENT DOCUMENTS

| | | | | |
|---|---|---|---|---|
| 3,914,058 A | * | 10/1975 | Knapp et al. | 356/427 |
| 4,172,524 A | * | 10/1979 | Holm et al. | 209/524 |
| 5,568,262 A | * | 10/1996 | LaChapelle et al. | 356/627 |

FOREIGN PATENT DOCUMENTS

JP          2001-201457          7/2001

* cited by examiner

Primary Examiner—Richard A. Rosenberger
Assistant Examiner—Vincent P. Barth
(74) Attorney, Agent, or Firm—Ladas & Parry LLP

(57) ABSTRACT

A turn controllable inspection table which have a step between a portion where mount sections on which respective objects being inspected are mounted are formed along a circumference and an inside portion thereof, so that light from a light source illuminating a side face portion of each object being inspected is allowed to be incident on at least a side face region including a bottom portion of a side face of each object being inspected in a direction perpendicular to the side face region is provided. Further, clamps for fixing the respective objects being inspected onto the mount sections by pressing a head portion of each object being inspected with a top board made of a transparent member, so that inspection is possible across an entire region from all directions including directions from above and sideways of each object being inspected are provided. Consequently, it is possible to provide an inspecting apparatus for a foreign matter capable of eliminating a blind spot in an illuminated region and a pictured region of an object being inspected, and capable of detecting the presence or absence of a suspended foreign matter inside a container as a an object being inspected at a high accuracy without stopping the production line, and an inspecting mechanism thereof.

6 Claims, 6 Drawing Sheets

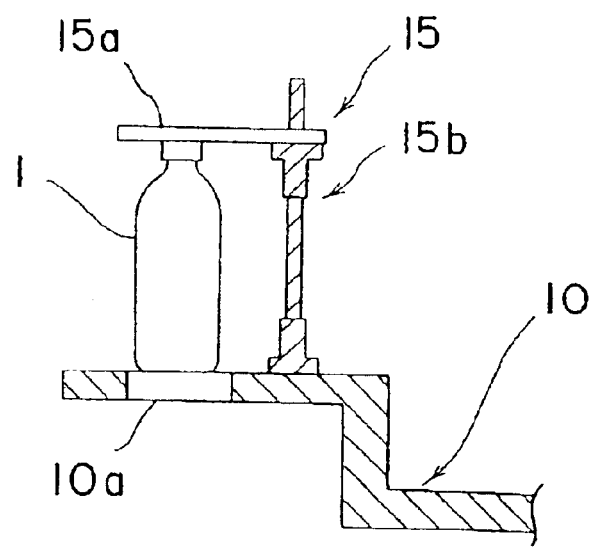
FIG. 3A
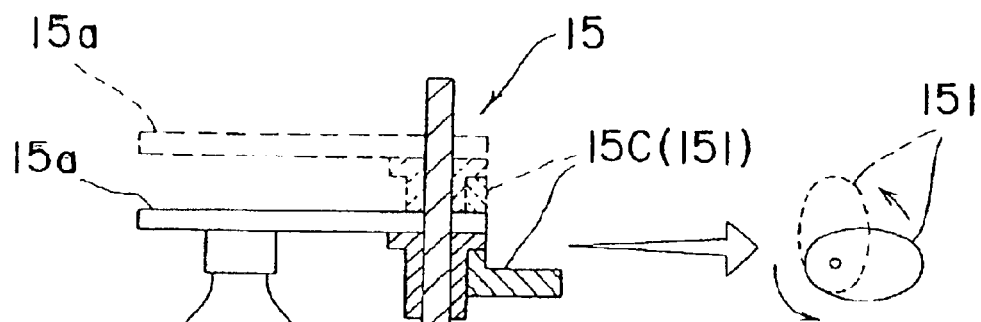
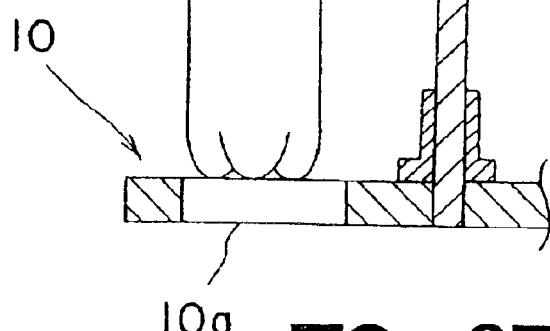
FIG. 3C
FIG. 3B

US 6,914,672 B2

INSPECTING APPARATUS FOR FOREIGN MATTER AND INSPECTING MECHANISM THEREOF

BACKGROUND OF THE INVENTION

1. Field of the Invention

The present invention relates to an inspecting apparatus for a foreign matter for optically detecting a foreign matter got entered an object being inspected, namely, a light-transmitting container, such as a bottle and a PET bottle, filled with a liquid product, such as liquid agents and drinks, and to an inspecting mechanism thereof, and more particularly to an inspecting apparatus for a foreign matter for detecting in real time a foreign matter got entered a container placed on an inspection table that rotates at a high speed in sync with a transportation speed of the container on production line and to an inspecting mechanism thereof.

2. Description of the Related Art

Adoption of the HACCP (Hazard Analysis Critical Control Point) system, which is highly evaluated across the world as a sanitary control system method, to the Food Sanitation Law and enforcement of the PL (Product Liability) Law in recent years have been making it mandatory to further ensure the product safety by forestalling a hazard, such as microbial contamination and entrance of foreign matters of other kinds, that could occur in any stage from manufacturing/processing of products, such as food and drugs, to consumption by end consumers through storage/distribution of the products.

Conventionally, in a production line of a manufacturing/processing factory for manufacturing liquid products (liquid agents, drinks, etc.), microbial contamination is prevented by sterilization with heating, and entrance of a foreign matter is prevented by removing the foreign matter with a cyclone separator. After the liquid product is filled in a container, such as a can and a bottle, final inspection is conducted by exploiting transmission or reflection of light. More specifically, when an object being inspected is a transparent container filled with a liquid, such as liquid agents and drinks, the object being inspected is pictured by a CCD camera, and digital image data thus obtained is processed by an image processing apparatus. Then, the presence or absence of a foreign matter got entered the liquid inside the container and the presence or absence of a flaw of the container are detected, whereby the conformity of the final product is automatically judged.

For example, as a method for detecting a foreign matter got entered a liquid agent or a drink inside a sealed container, such as an ampoule, there is known a foreign matter detecting method, by which a cylindrical container is rotated at a high speed (for example, at 6000 rpm approximately) in an upright posture and stopped after a foreign matter is forced upward, and the foreign matter falling downward is shot by a camera, so that the foreign matter is detected from the trail of movements. As has been described, in a case where the container is made of a light-transmitting member and is filled with a transparent (including translucent) liquid, it is possible to inspect the inside of the container by picturing the container with a CCD camera or the like and carrying out image processing even after the container is sealed.

Also, as an inspecting system for a deposited foreign matter inside the container, there is a system described in Japanese Patent Laid-Open No. 2001-201457 filed by the applicant of the present application. FIG. 5 is a plan view showing an arrangement of a major portion of an inspecting system for a foreign matter described in this publication. PET bottles filled with drinks, such as soft drinks and juice, on a production line are transported successively at regular intervals in a direction indicated by an arrow A of FIG. 5 on a linearly moving transportation conveyer 22 by rotations of a screw (worm gears) 21. An inspecting mechanism unit 30 for inspecting the PET bottles for a foreign matter is provided with an inspection table 31 including carrying in/carrying out star wheel boards 32 and 33 linked to the transportation conveyer 22 and a large-diameter star wheel board for use in inspection. Each PET bottle flowing into the inspecting mechanism unit 30 is transported by these transportation means along paths R1, R2, and R3 of FIG. 5. The inspecting mechanism unit 30 is arranged to inspect in real time the respective PET bottles being transported along the path R2 at a high speed (approximately 1200 bottles/min.) for foreign matters deposited inside.

According to the inspecting system described above, mount sections (inspection section) 31a, on which respective objects being inspected are sequentially mounted in an upright posture, are formed along the circumference of the inspection table 31 that is driven rotationally. Each of the mount sections 31a is formed from a filter made of a light-transmitting member, such as resin and glass. Each of the mount sections 31a is provided with restraining means for an object being inspected formed of a holding mechanism 34 as shown in FIG. 6, for example. A PET bottle 1 mounted on the mount section 31a is fixed thereto by being held with the holding mechanism 34 at the side face portions, and is transported along the path R2 of FIG. 5. FIG. 7 is a view showing an example of an arrangement as to the placement of illuminating means and imaging means to detect a deposited foreign matter. According to this example, first illuminating means 35 having a ring of light emitting portion is provided above the filter (the mount section) 31a, and a light emitting portion of second illuminating means 35 and a light receiving portion of imaging means 36 are provided under the filter 31a. Then, objects being inspected 1, which are held by the holding mechanisms 34 at either side of the side face or sandwiched by a belt or the like, are being transported successively in an upright posture along the annular path R2 of FIG. 5, whereby the containers are inspected successively for foreign matters inside based on image information from a plurality of inspection cameras 36.

Incidentally, as has been described, detecting a foreign matter by the trail of the foreign matter that is forced upward and then allowed to fall downward by rotating the object being inspected is known as a method for detecting a foreign matter in the liquid inside a sealed container. However, this method has a problem that detection is impossible when a foreign matter has too large specific gravity to be forced upward by rotations or a foreign matter is a suspended foreign matter that does not fall downward. Also, inspection takes too long with the method for detecting a foreign matter by observing the trail of the foreign matter falling downward based on pictured image data. Hence, this method may not be applicable to an inspecting system for products mass-produced at a high transportation speed.

On the contrary, the system described in Japanese Patent Laid-Open No. 2001-201457 is applicable as an inspecting system for products mass-produced at a high transportation speed, because it can successively inspect objects being inspected that are being transported at a high speed. However, this system is intended to chiefly detect a deposited foreign matter, and a suspended foreign matter that does not deposit has to be detected by another inspecting mechanism. Even if an imaging camera and a illuminating apparatus for detecting a suspended foreign matter are provided to inspect objects being inspected for both the deposited and suspended foreign matters by a single inspecting mechanism, when the entire side face of the object being inspected is pictured by the conventional inspecting mechanism, there arises a problem that a slot pitch portion of the wheel for fixing the object being inspected placed on the inspection star wheel or a portion of the holding mechanism blocks illuminating light, or such a portion comes into the field of view of the imaging camera. If the illuminating means and the imaging means are placed so as to avoid the slot pitch portion of the wheel or the portion of the holding mechanism, irregular reflection occurs due to an angle of incidence of the illuminating light on the object being inspected or the shape of the container, and such adverse effects make the detection of a foreign matter less accurate. Hence, it is difficult to inspect the object being inspected entirely by a single inspecting mechanism at high accuracy. Further, in the case of detecting a foreign matter in the liquid by illuminating the side face portion of the object being inspected placed on the inspection table by the illuminating means placed behind the object being inspected and picturing the side face region by the imaging means placed in front of the object being inspected, there is a blind spot in the illuminated region (or the pictured region) at the bottom portion of the side face of the object being inspected, which poses a problem that a foreign matter present within the blind spot cannot be detected.

SUMMARY OF THE INVENTION

The present invention is devised in view of the foregoing, and has an object to provide an inspecting apparatus for a foreign matter capable of eliminating a blind spot in an illuminated region and a pictured region of an object being inspected, and capable of detecting the presence or absence of a suspended foreign matter inside a container as an object being inspected at high accuracy without stopping a production line, and an inspecting mechanism thereof.

The present invention relates to an inspecting mechanism for a foreign matter for optically detecting a foreign matter got entered respective objects being inspected filled with a liquid product, and the object of the present invention is achieved by including a turn controllable inspection table which have a step between a portion where mount sections on which the respective objects being inspected are mounted are formed along a circumference and an inside portion thereof, so that light from a light source illuminating a side face portion of each object being inspected is allowed to be incident on at least a side face region including a bottom portion of a side face of each object being inspected in a direction perpendicular to the side face region. The object of the present invention is achieved more effectively by further including: illuminating means, provided at an inside portion of the mount sections, for illuminating an entire side face of each of the objects being inspected that are being transported in association with turns of the inspection table in a direction perpendicular to the side face; and imaging means, provided at an outside of the mount sections so as to be able to picture a suspended foreign matter forced to move toward a side face wall portion of each object being inspected by a centrifugal force derived from the turns of the inspection table, for picturing the entire side face of each of the objects being inspected that are being transported.

Also, the object of the invention is achieved by including: a turn controllable inspection table which have mount sections formed along a circumference thereof for the respective objects being inspected; and clamps for fixing the respective objects being inspected onto the mount sections by pressing a head portion of each object being inspected with a top board made of a transparent member, so that inspection is possible across an entire region from all directions including directions from above and sideways of each object being inspected. Further, the object of the invention is achieved more effectively by arranging in such a manner that each of the clamps includes: the top board made of the transparent member; a supporting member, provided to each of the mount sections, for supporting the top board from outside of an inspection field of view for the entire region subject to inspection so that the top board is allowed to slide vertically; and a mechanism for moving the top board up and down in sync with carrying-in timing of the respective objects being inspected onto the mount sections.

Also, an inspecting apparatus for a foreign matter is achieved by including: a turn controllable inspection table which have mount sections made of a transparent member and formed along a circumference thereof; restraining means for restraining the respective objects being inspected onto the mount sections by pressing a head portion of each object being inspected with a top board made of a transparent member; illuminating means for illuminating an entire side face of each of the objects being inspected that are being transported in association with turns of the inspection table; imaging means for picturing the entire side face of each of the objects being inspected that are being transported; and inspecting means for detecting a suspended foreign matter based on an image signal from the imaging means. Further, the object of the invention is achieved more effectively by arranging in such a manner that the inspection table is provided with a step between a portion where the mount sections are formed along the circumference and an inside portion thereof, so that a beam of light from the illuminating means is allowed to be incident on at least a side face region including a bottom portion of a side face of each object being inspected in a direction perpendicular to the side face region.

BRIEF DESCRIPTION OF THE DRAWINGS

The above and other objects will become more apparent when a preferred embodiment of the invention is considered in connection with the drawings, in which:

FIGS. 3A through 3C are side views schematically showing an example of a clamping mechanism of the invention;

DETAILED DESCRIPTION OF THE PREFERRED EMBODIMENTS

The following description will describe in detail a preferred embodiment of the invention with reference to the accompanying drawings. In the following description, a cylindrical container filled with a liquid product will be explained as an example of an object being inspected. It should be appreciated, however, that the shape of the container, such as a bottle or a PET bottle, is not limited to a cylindrical shape, and the object being inspected may be a polygonal or flat container.

Figure 1:
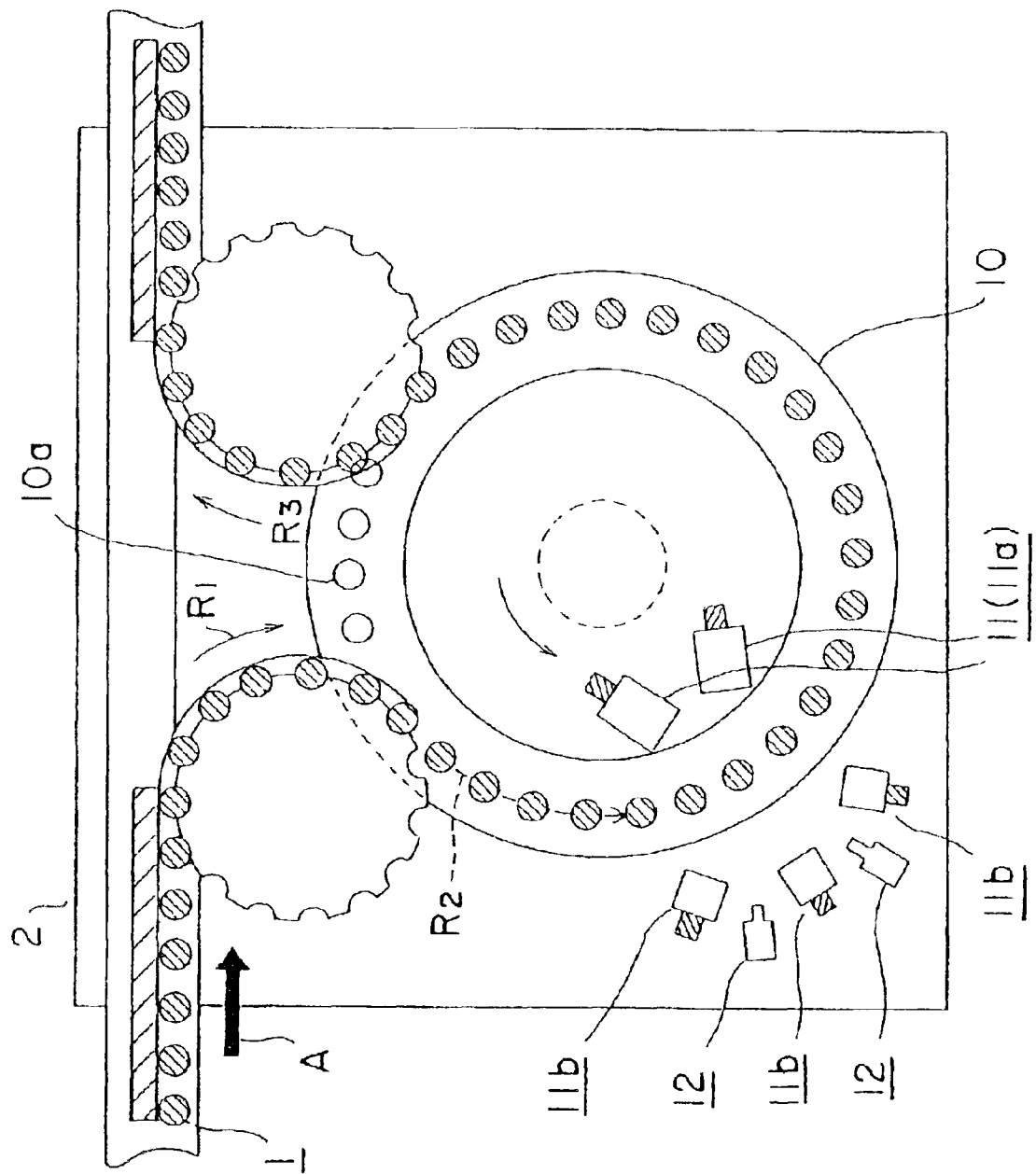
FIG. 1 is a partial cross-sectional side view showing an example of an arrangement of an inspecting mechanism unit in an inspecting apparatus for a foreign matter of the invention.
Figure 2:
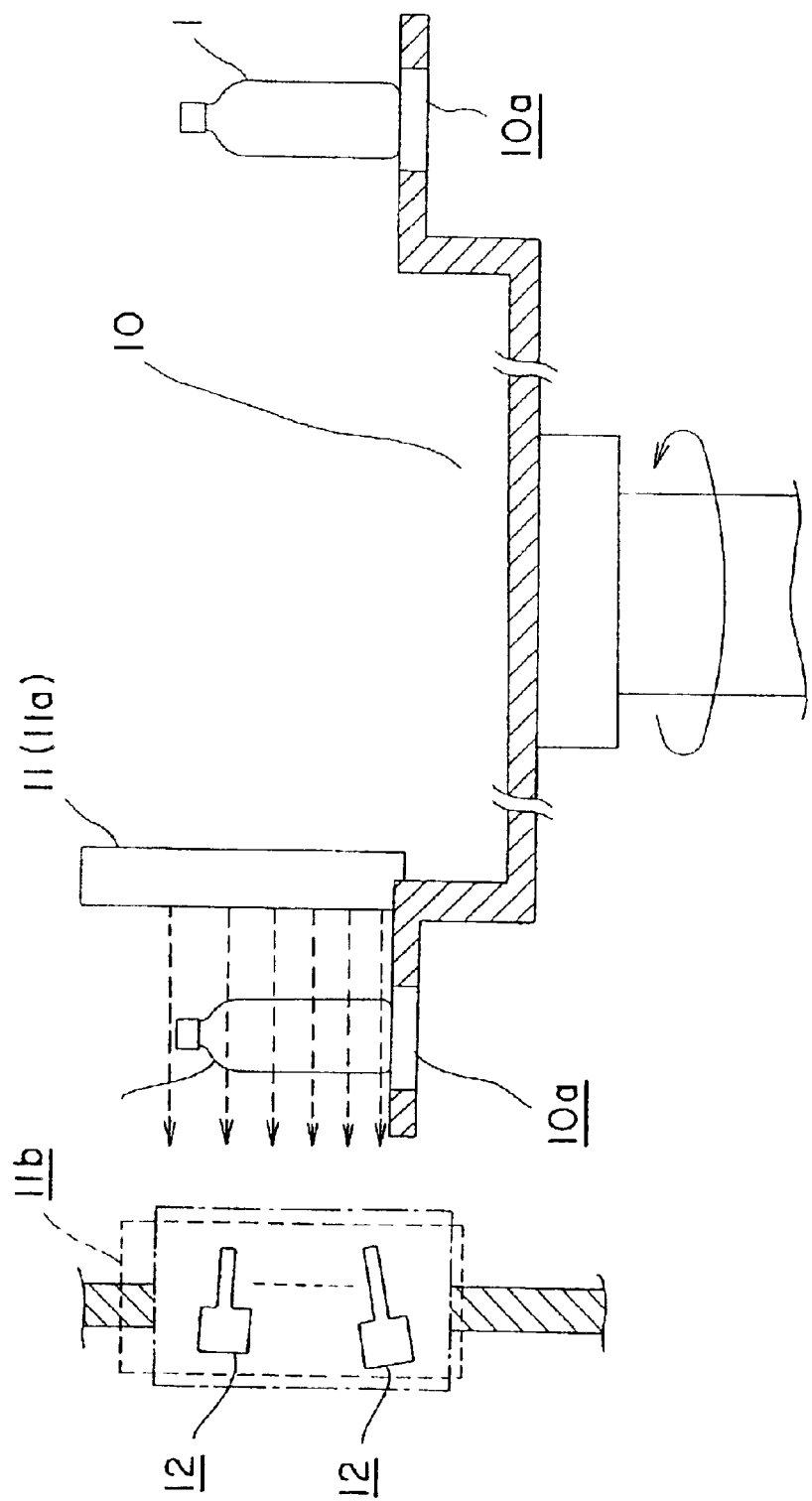
FIG. 2 is a partial cross-sectional side view showing an arrangement of the inspecting mechanism unit of FIG. 1.
Figure 5:
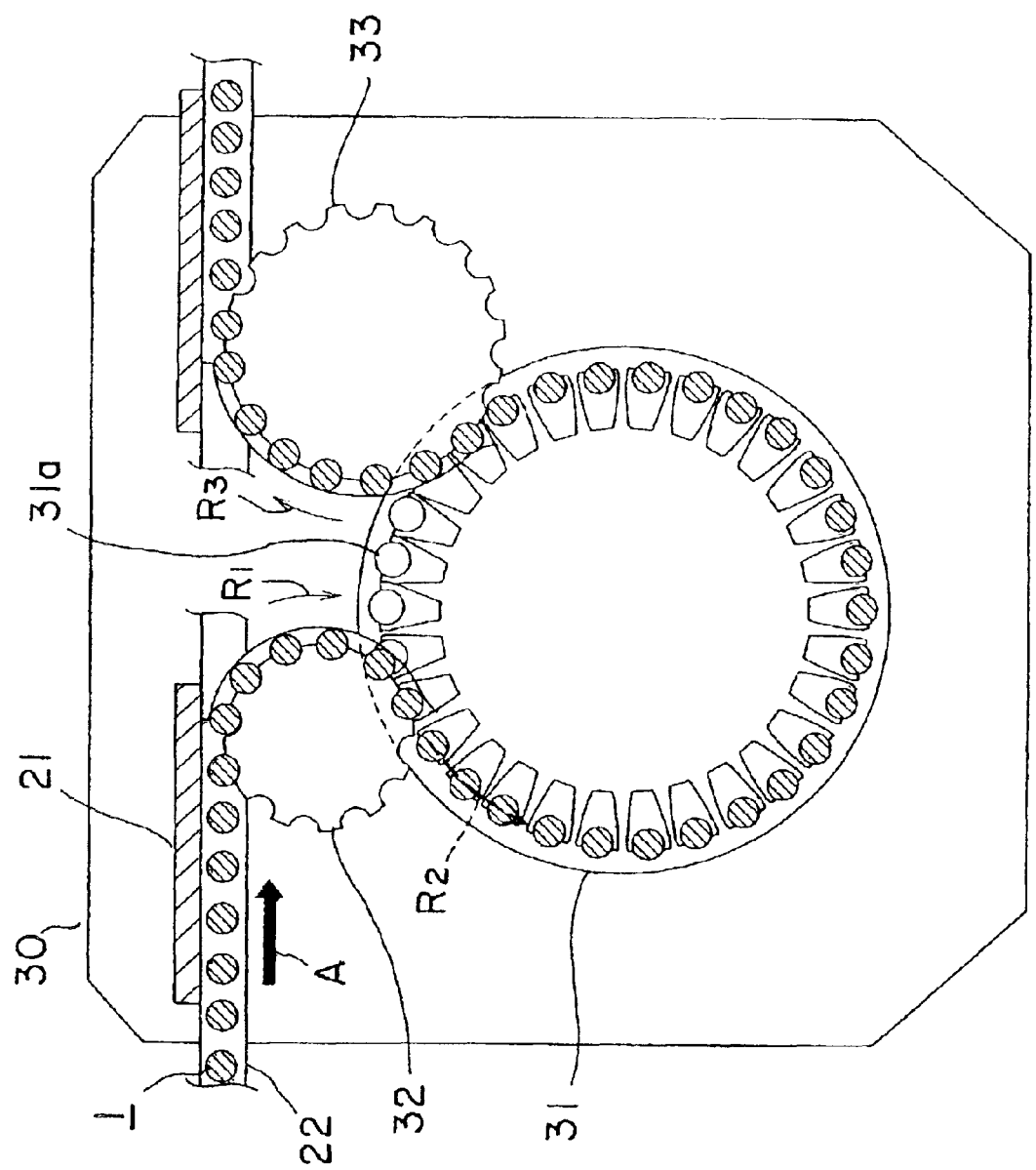
FIG. 5 a plan view showing an example of an arrangement of a major portion of a conventional inspecting system for a foreign matter.
Figure 6:
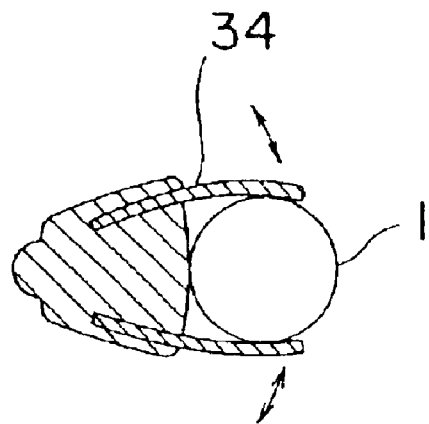
FIG. 6 is a plan view showing an example of an arrangement of restraining means in the conventional inspecting system for a foreign matter.

FIG. 1 is a plan view showing an example of an arrangement of an inspecting mechanism unit 2 in an inspecting apparatus for a foreign matter of the invention in correspondence with FIG. 5. FIG. 2 is a partial cross-sectional side view showing an arrangement of the inspecting mechanism unit 2 of FIG. 1. Referring to FIG. 1, an inspection table 10 includes a star wheel board rotating at a high speed in sync with a speed of objects being inspected 1 that are flowing down a production line on a transportation conveyer, so that the presence or absence of a foreign matter (herein, a suspended foreign matter) got entered the respective objects being inspected 1 is detected on the single inspection table 10 in real time without stopping the production line on one hundred percent inspection basis. As shown in FIG. 2, illuminating means 11a is provided on the inside portion of the inspection table 10 of the invention, and a step is made between a portion where mount sections 10a are formed along the circumference and an inside portion thereof, so that a beam of light from the illuminating means 11a is allowed to be incident on at least a side face region including the bottom portion of the side face of each object being inspected 1 in a direction perpendicular to the side face region. In other words, the inspection table 10 is a 2-stage table having the inside portion formed lower than the mount sections 10a, so that a light emitting face at the end portion of the illuminating means 11a is positioned lower than the mount faces of the mount sections 10a.

The illuminating means (hereinafter, referred to as first illuminating means) 11a described above is illuminating means for illuminating the entire side face of each of the objects being inspected 1 that are being transported in association with turns of the inspection table 10 by emitting substantially uniform planar light in a direction perpendicular to the side face, and is formed of one or more than one flat light or the like. Also, second illuminating means 11b for illuminating the entire side face of each object being inspected 1 by emitting planar light from the front is provided at the outside portion of the inspection table 10. Hence, the entire side face of the object being inspected 1 is illuminated by both the first illuminating means 11a for producing transmitted light and the second illuminating means 11b serving as auxiliary illuminating means for producing reflected light.

Also, imaging means 12 for detecting a foreign matter (mainly, a suspended foreign matter) in the liquid by picturing the entire side face portion of each of the objects being inspected 1 that are being transported is provided at the outside of the mount sections 10a of the inspection table 10. The imaging means 12 is formed of one or more than one CCD sensor or the like, and supported on the axis so that it is allowed to move up and down in the vertical direction and to rotate in the horizontal direction, and is also supported on the axis so that an angle in the horizontal direction is adjustable. In the present example, a total of eight imaging cameras 12 are placed in four vertical stages in the horizontal direction as shown in FIG. 1 to picture the entire object being inspected 1 from sideways. The position and the angle of these imaging cameras 12 are adjusted in response to the height and shape of the objects being inspected manually or under the control of an outside apparatus, and these imaging cameras 12 are used selectively (for example, those at the second and fourth stages in each column are selected for use in picturing). The imaging means 12 pictures a suspended foreign matter forced to move toward the side face wall portion of the object being inspected 1 by a centrifugal force derived from the turns of the inspection table 10, which makes it possible to detect a suspended foreign matter got entered the liquid inside the object being inspected 1 or a foreign matter adhering to the inner wall face of the container at high accuracy.

Also, restraining means 15 for restraining the object being inspected 1 on the mount section 10a by pressing the head portion thereof with a top board 15a as shown in FIG. 3A at the timing the object being inspected 1 is carried into the inspecting mechanism unit 2 and mounted on the mount section 10a of the inspection table 10 is provided above each of the mount sections 10a formed along the circumference of the inspection table 10. The top board 15a, one of the components of the straining means 15, is made of a transparent member, such as acrylic, and an end portion of the top board 15a is supported by a supporting member 15b from the outside of the inspection field of view, so that the entire region can be optically inspected from all directions by providing the light emitting portion and the light receiving portion at arbitrary positions, that is, above, sideways, and under the object being inspected 1. The object being inspected 1 is sandwiched by the transparent top board 15a and the mount section 10a made of a transparent member, such as hard glass, thereby being fixed onto the inspection table 10. Both the top boards 15a and the mount sections 10a are made of a light-transmitting member serving also as an optical filter that prevents irregular refection by absorbing light incident on with an angle.

FIGS. 3B and 3C are views schematically showing an example of a clamping mechanism employed as the restraining means. A clamp 15 as an example of the restraining means is provided with the top board 15a made of a transparent member, the supporting member 15b for supporting the top board 15a from the outside of the inspection field of view so that it is allowed to move up and down by sliding vertically, and a mechanism 15c for moving up and down the top board 15a in sync with the timing the object being inspected 1 is mounted on the mount section 10a. Both the transparent top board 15a and the transparent mount section 10a restrain the object being inspected 1 so as to be fixed onto the mount section 10a. In the present example, the top board 15a and the supporting member 15b are provided to each mount section 10a. The mechanism 15c that moves the top board 15a up and down includes an eccentric cam 151 as shown in FIG. 3C, for example, and is provided to each supporting member 15b. By allowing the top board 15a to fall downward by its own weight (or pushed downward by a spring or the like) at the carrying-in timing to the mount section 10a in association with rotations of the eccentric cam 151 in sync with the speed of the objects being inspected 1 that are being transported in association with the turns of the inspection table 10, each of the objects being inspected 1 successively carried onto the inspection table 10 from the upstream transportation path of the inspecting mechanism unit 2 is fixed by the respective top boards 15a, and transported along the annular path of the inspection table 10. Then, the top board 15a is moved upward immediately before the object being inspected 1 is carried out from the mount section 10a by the carrying-out star wheel board. The mechanism 15c that moves the top board 15a up and down may be replaced with another mechanism; for example, it may include an arched guide plate whose height is adjustable in response to the size (height) of the objects being inspected. More specifically, it may be arranged in such a manner that an arched guide member (for example, an arched guide member forming an arc in the horizontal direction and forming an arc also in the vertical direction along the annular path from the carrying-out portion to the carrying-in portion of the annular path R2 of FIG. 1) may be provided at a predetermined position in the inspection table 10, so that the top board 15a is allowed to move up and down by sliding a part of the supporting member 15b of the top board 15a on the guide member along the curved face in the vertical direction.

Figure 4:
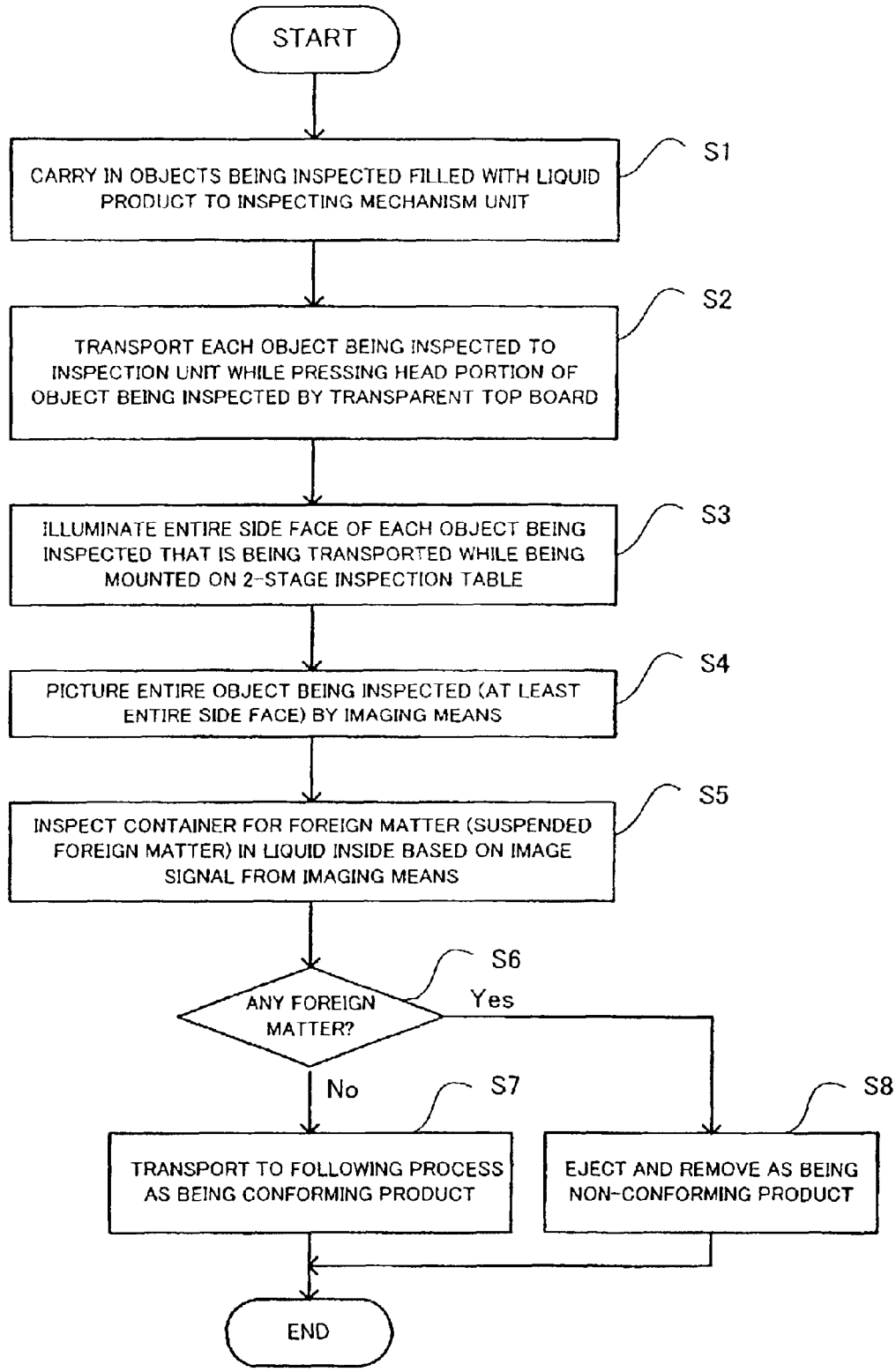
FIG. 4 is a flowchart detailing an example of operations of the inspecting apparatus for a foreign matter of the invention.

The following description will describe an example of operations of the inspecting apparatus for a foreign matter of the invention arranged as above with reference to the flowchart of FIG. 4.

The respective objects being inspected 1, which are filled with a liquid product on the production line and flowing down on the transportation conveyer, are carried into the inspecting mechanism unit 2 by the transportation mechanism formed of the carrying-in star wheel board or the like (Step S1), and sequentially mounted on the respective mount sections 10a of the inspection table 10, which is one of the components of the inspecting mechanism unit 2. At this point, in the inspecting apparatus for a foreign matter, the top board 15a is allowed to fall downward to the head portion of the object being inspected 1 by the clamping mechanism at the timing the object being inspected 1 is mounted on the mount section 10a, so that the object being inspected 1 is transported along the annular path while being fixed onto the mount section 10a by the pressing of the top board 15a (Step S2). Subsequently, in the control unit of the inspecting apparatus for a foreign matter, the illuminating means 11a for producing transmitted light provided at the lower step side of the 2-stage inspection table 10 irradiates light to the entire side face of the object being inspected 1 in a direction perpendicular to the side face portion thereof, and the illuminating means 11b for producing reflected light provided in front (at the side of the imaging camera) of the object being inspected 1 irradiates light to the entire side face of the object being inspected 1, whereby the object being inspected 1 is illuminated entirely (Step S3). Then, the imaging means 12 pictures the object being inspected 1 entirely from the side face (herein, a plurality of imaging cameras picture the entire side face portion from all directions) (Step S4), whereby a suspended foreign matter is detected based on an image signal from the imaging means 12.

The inspection procedure described as above is carried out by detecting a change in intensity in an area subject to inspection excluding an edge portion (a portion appearing as a pattern in the image) formed by a unique shape of the object being inspected 1, for example, by the outside control apparatus or the control unit incorporated in the inspecting apparatus (Step S5). Then, in Step S6, the fixing state of the object being inspected 1 is released by moving the top board 15a upward, so that it is carried out onto the transportation conveyer by the carrying-out mechanism formed of the carrying-out star wheel board or the like, and the object being inspected 1 judged as a conforming product having no foreign matter as a result of the inspection is transported further to proceed to the following process (Step S7). On the other hand, in case that a foreign matter is detected, after the object being inspected 1 is carried out onto the transportation conveyer, the object being inspected 1 is pushed instantaneously at the side face portion and ejected onto a removing conveyer by a removing mechanism using a knock-out brush or a removing mechanism using a flip-down cylinder provided with an elastic member at the end portion of the piston, whereby the object being inspected 1 is removed as a non-conforming product (Step S8).

The result of the inspection (information of the conforming/non-conforming product, non-conforming product data, etc.) is sent to an unillustrated FA (Factory Automation) server system, for example, and recorded in real time in a database in connection with the manufacturing information. This allows the central supervision/control computer or a terminal device having an access to the database through a network, such as a LAN and an internet, to immediately analyze each inspection status and find out how the foreign matter got entered.

Figure 7:
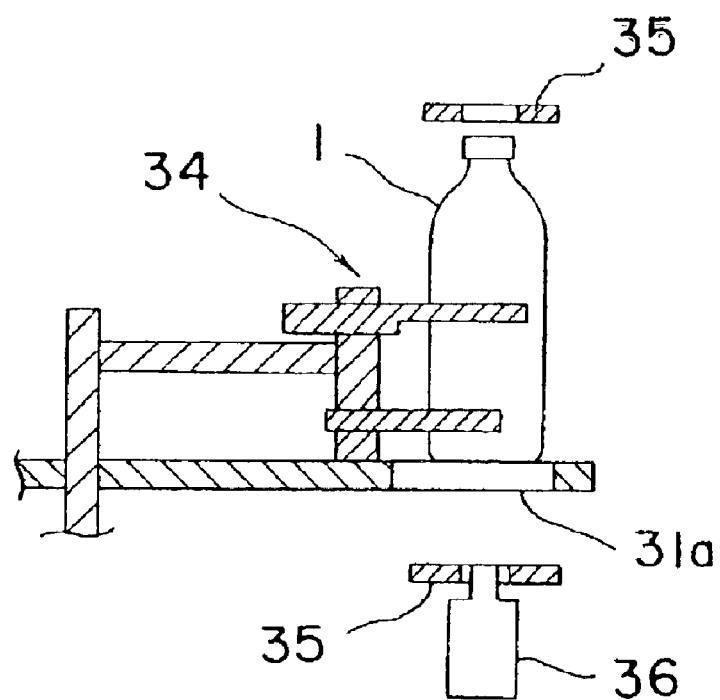
FIG. 7 is a partial cross-sectional side view showing an example of an arrangement as to placement of illuminating means and imaging means to detect a deposited foreign matter in the conventional inspecting system for a foreign matter.

The embodiment described above was the case of inspection for a suspended foreign matter. However, it may be arranged to detect a deposited foreign matter by the same inspecting mechanism unit 2 by placing the illuminating means and the imaging means (for example, the illuminating means 35 and the imaging means 36 of FIG. 7) for detecting a deposit foreign matter at the downstream of the annular transportation path of FIG. 1.

As has been described, according to the invention, it is possible to eliminate a blind spot in the illuminated region and the pictured region of the object being inspected, thereby making it possible to detect a foreign matter got entered the object being inspected at high accuracy. Also, because the inspection table is of a 2-stage structure so that light can be irradiated to the object being inspected in a direction perpendicular to the side face region including the bottom portion of the object being inspected, it is possible to inspect a microscopic region in the bottom portion of the object being inspected as well at high accuracy. Further, because not only a suspended foreign matter but also a deposited foreign matter inside the container can be detected on the same inspection table without stopping the production line for all the objects being inspected that are being transported at a high speed, both the cost and installation space of the inspecting mechanism can be saved.

Obviously many modifications and variations of the invention are possible in the light of the above teachings. It is therefore to be understood that within the scope of the appended claims in the invention may be practiced otherwise than as specifically described.

What is claimed is:

1. An inspecting device for optically detecting foreign matter in a liquid deposited in translucent containers, said inspection device comprising:
   a turn controllable inspection table having mount sections around a rotation axis on which said containers are mounted; and
   illuminating means illuminating an entire side face of a container on said mount sections from sideways, the container being transported along an annular path in association with turns of said inspection table;
   wherein:
   (i) said inspection table comprises a two-stage structure forming a step between a circumferential portion where the mount sections are formed and an inside portion thereof, wherein the inside portion is lower than the circumferential portion;

(ii) said illuminating means provides a flat flight emitting a substantially uniform planar light of parallel rays from a light emitting face, and having a structure emitting a perpendicular beam of light to each side face of said container from plural side directions of said container by a plurality of said flat lights so that the entire side face of said container is illuminated; and (iii) said plurality of said flat lights are positioned on the inside portion of the inspection table, and a bottom end portion of the light emitting face of said plurality of flat lights is positioned lower than a bottom portion of said container on said mount sections so that a blind spot is eliminated in the illuminated region of the bottom portion of said container.

2. The inspecting device according to claim 1, further comprising:

imaging means, provided outside of said mount sections to be able to picture suspended foreign matter forced to move toward a side face wall portion of said container by a centrifugal force generated by turns of said inspection table, for picturing the entire side face of said container illuminated by said illuminating means.

3. An inspecting device for optically detecting foreign matter in a liquid deposited in translucent containers, wherein said inspecting device comprises:

(i) a turn controllable inspection table having mount sections around a rotation axis and being made of a light-transmitting member serving also as an optical filter for preventing irregular reflection; and (ii) clamps for fixing said containers onto said mount sections by pressing head portions of said containers transported onto said inspection table continuously from an upstream transportation path with a top board formed by a transparent member serving also as an optical filter for preventing irregular reflection, so that inspection is possible across an entire region from all directions including directions from above and sideways of said container.

4. The inspecting device according to claim 3, wherein each of said clamps comprises:

said top board;

a supporting member provided to each of said mount sections for supporting said top board from outside of an inspecting field of view for said entire region so that said top board is allowed to slide vertically; and a mechanism for moving said top board up and down in sync with carrying-in timing of said containers onto said mount sections.

5. An inspecting device for optically detecting foreign matter in a liquid deposited in translucent containers, wherein said inspecting device comprises:

(i) a turn controllable inspection table having mount sections around a rotation axis made of a light-transmitting member serving also as optical filters for preventing irregular reflection;

(ii) restraining means for restraining said containers by pressing head portions thereof by top boards made by a transparent member serving also as optical filters for preventing irregular reflection;

(iii) first illuminating means for illuminating an entire side face of said containers transported in association with turns of said inspection table;

(iv) first imaging means for picturing an entire side face of containers illuminated by said first illuminating means;

(v) second illuminating means for illuminating said containers transported in association with turns of said inspection table from above of the top boards serving also as an optical filter;

(vi) second imaging means for picturing said container illuminated by said second illuminating means from below of said mount section serving as an optical filter; and (vii) inspecting means for inspecting foreign matter including suspended matter and deposited foreign matter in a liquid deposited in said containers based on image signals obtained from said first and second imaging means.

6. An inspecting device for inspecting foreign matter according to claim 5, wherein:

said inspection table comprises a two-stage structure forming a step between a circumferential portion where mount sections are formed and an inside portion thereof, wherein the inside portion is lower than the circumferential portion; and said first illuminating means is positioned on a lower stage of the inspection table, and the bottom end portion of the emitting face is positioned lower than the bottom portion of said containers on said mount sections.

* * * * *